United States Patent [19]
Ito

[11] Patent Number: 5,162,863
[45] Date of Patent: Nov. 10, 1992

[54] METHOD AND APPARATUS FOR INSPECTING A SPECIMEN BY OPTICAL DETECTION OF ANTIBODY/ANTIGEN SENSITIZED CARRIERS

[75] Inventor: Yuji Ito, Chigasaki, Japan

[73] Assignee: Canon Kabushiki Kaisha, Tokyo, Japan

[21] Appl. No.: 563,853

[22] Filed: Aug. 8, 1990

Related U.S. Application Data

[63] Continuation of Ser. No. 304,236, Jan. 31, 1989, abandoned.

[30] Foreign Application Priority Data

| Feb. 15, 1988 | [JP] | Japan | 63-033482 |
| Apr. 22, 1988 | [JP] | Japan | 63-100571 |
| Jul. 12, 1988 | [JP] | Japan | 63-173579 |

[51] Int. Cl.$^5$ ............ G01N 15/14; G01N 33/547; G01N 33/551; G01N 33/552
[52] U.S. Cl. ............ 356/73; 356/336; 356/343; 436/523; 436/533; 436/805; 436/807
[58] Field of Search ............ 356/73, 336, 343, 36; 436/523, 533, 534, 805, 807

[56] References Cited
U.S. PATENT DOCUMENTS 4,521,521 6/1985 Abbott ............ 356/336
4,747,685 5/1988 Suzuki ............ 356/36
4,960,714 10/1990 Hadfield et al. ............ 436/533

FOREIGN PATENT DOCUMENTS 0070527 1/1983 European Pat. Off.
2319131 2/1977 France.
2123146 1/1984 United Kingdom.

OTHER PUBLICATIONS

Patent Abstracts of Japan, vol. 11, No. 285 (P-616) [2732], Sep. 16, 1987.

Primary Examiner—Vincent P. McGraw
Attorney, Agent, or Firm—Fitzpatrick, Cella, Harper & Scinto

[57] ABSTRACT

In a method and an apparatus wherein carriers sensitized by an antibody or an antigen are caused to react to a specimen sample and the condensation of the carriers caused by the antigen-antibody reaction is optically detected by the use of flow cytometry, thereby measuring the antigen or antibody in the specimen sample, a plurality of kinds of carriers differing in optical characteristic are sensitized by different kinds of antibodies or antigens, respectively, whereby a plurality of kinds of antigens or antibodies in the specimen sample are measured at a time.

69 Claims, 7 Drawing Sheets

METHOD AND APPARATUS FOR INSPECTING A SPECIMEN BY OPTICAL DETECTION OF ANTIBODY/ANTIGEN SENSITIZED CARRIERS

This application is a continuation of application Ser. No. 07/304,236 filed Jan. 31, 1989, now abandoned.

BACKGROUND OF THE INVENTION

1. Field of the Invention

This invention relates to the field of antigen-antibody reaction measurement using a carrier such as latex which is utilized in the field of immunology.

2. Related Background Art

Heretofore, as an immunity inspecting method, use has been made of a method in which a suspension comprising a mixture of a carrier such as latex sensitized by a predetermined antibody and a specimen sample is prepared and where an antigen to be specified is contained in the specimen sample, an antigen-antibody reaction occurs between the antigen and the sensitized antibody and carrier particles are coupled together and the presence of the antigen in the specimen sample or the amount of the antigen is measured from the condensed state of the carrier. In that case, a method of discriminating the condensed state of the carrier has been carried out by measuring the absorbance of the suspension including the carrier or the degree of light scattering of the suspension. Particularly, by the use of flow cytometry, that is, by wrapping the suspension in sheath liquid, hydrodynamically converging it, causing individual carriers to flow to an inspecting position in succession, applying a light beam to the carrier at the inspecting position and judging the size of the carrier from the intensity of scattered light, it has been possible to judge the condensed state of the individual carriers and calculate the presence of the antigen or the amount of the antigen and accomplish highly accurate measurement. A specific example of it is described, for example, in U.S. Pat. No. 4,521,521. However, in the above-described example of the prior art, only a carrier sensitized by one kind of antibody can be used and only the inspection of one kind of antigen can be effected at a time, and this has formed a hindrance in enhancing the efficiency during mass medical examination.

As an example of the method of solving this problem, a method in which a plurality of kinds of fine particles differing in the kind of fluorescence or the particle diameter are used to measure a plurality of kinds of antigen-antibody reactions at a time is described in Japanese Laid-Open Patent Application No. 62-81567. According to this method, discrimination between the kinds of the fine particles is done by the fluorescence wavelength or a combination of the fluorescence wavelength and the particle diameter. If the particle diameter is only made to differ for a plurality of kinds of particles, the kinds of the particles cannot be distinguished in the case of a condensed state of the same size and therefore, it is necessary to distinguish between them by the fluorescence. However, the intensity of the fluorescence which occurs is weak and therefore, it has been difficult to reliably discriminate between the kinds of the particles from the fluorescence. Further, with an optical system for detecting scattered light, a precise optical system for detecting the weak fluorescence has been separately necessary.

SUMMARY OF THE INVENTION

It is an object of the present invention to provide a specimen inspecting method and a specimen inspecting apparatus which can simply measure the presence or the amount of a plurality of kinds of particular antigens or antibodies in a specimen at a time by the use of a plurality of kinds of carriers differing in optical characteristic.

It is another object of the present invention to provide a specimen inspecting method and a specimen inspecting apparatus which can reliably measure the presence or the amount of a plurality of kinds of particular antigens or antibodies in a specimen at a time by a simple construction without the use of fluorescence.

BRIEF DESCRIPTION OF THE DRAWINGS

FIGS. 6a to 8c show the results of the measurement of a plurality of kinds of latexes of different absorbances and of the same size.

FIGS. 9a to 11c show the results of the measurement of a plurality of kinds of latexes of different absorbances and different sizes.

FIG. 12 is a cytogram in which FIGS. 6 to 8 are arranged into one.

FIG. 13 is a cytogram in which FIGS. 9 to 11 are arranged into one.

DESCRIPTION OF THE PREFERRED EMBODIMENT

In the present embodiment, a plurality of kinds of latexes differing in absorbance are used as a plurality of kinds of carriers. However, this is not restrictive, but use may also be made, for example, of inorganic oxides such as silica, silica-alumina and alumina, mineral powder, metals, blood cells, staphylococci, cell-wall pieces, liposome, etc., and these may be combined to prepare a plurality of kinds of carriers differing in absorbance. To sensitize the carriers by an antibody, there are known a method of causing the antibody to be physically adsorbed, and a method of causing the antibody to be chemically adsorbed by the utilization of the functional groups on the carriers.

Figure 1A:
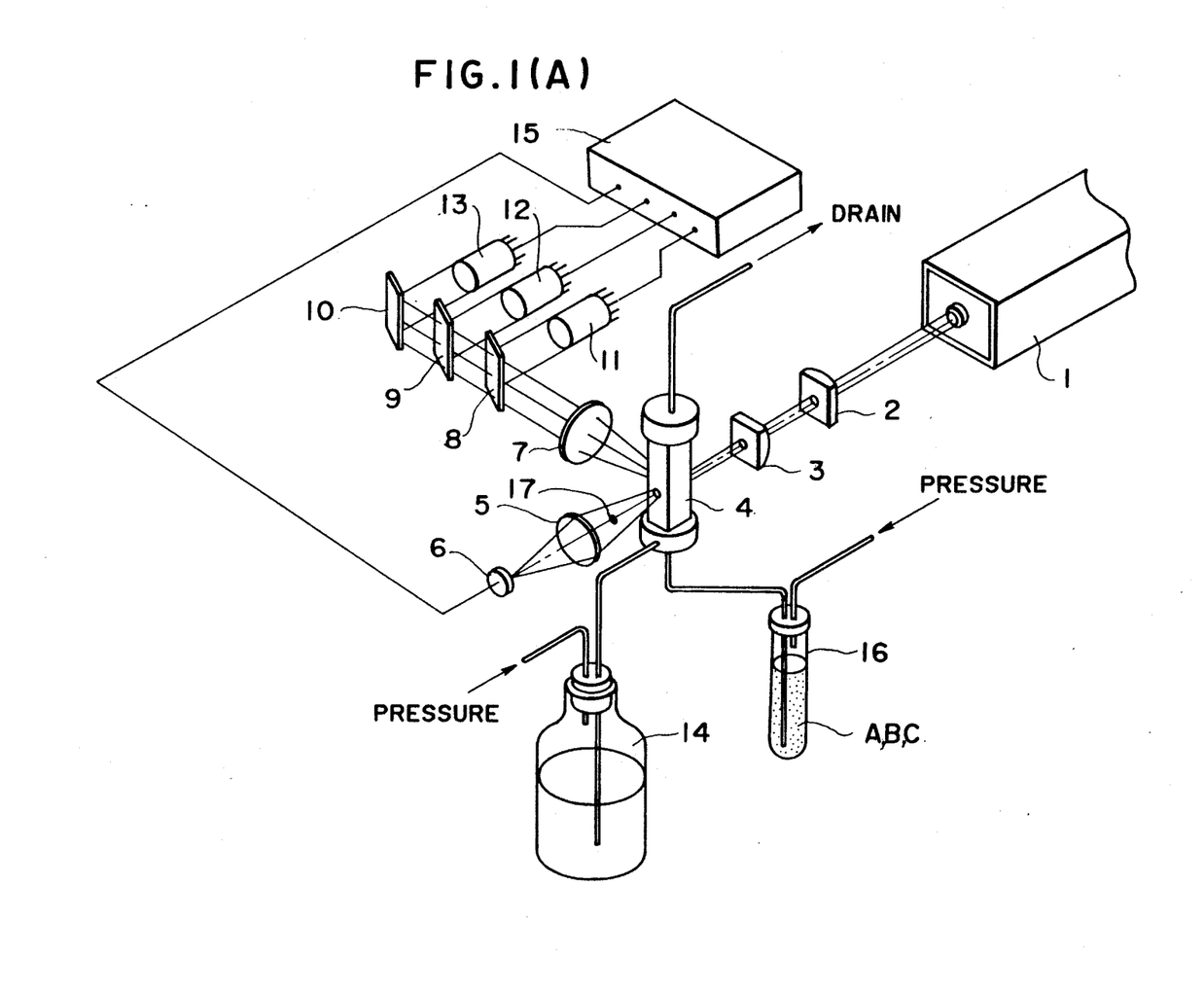
FIG. 1(A) shows the construction of an embodiment of the present invention.

As an example, a sample fluid in which a specimen sample such as man's serum is added to a mixture of a plurality of kinds of latexes A, B and C sensitized by three kinds of antibodies a, b and c, respectively and is adjusted to an appropriate reaction time and concentration is put into the sample fluid container 16 of FIG. 1(A). A specific example of adjusting the sample fluid is described, for example, in the aforementioned Japanese Laid-Open Patent Application No. 62-81567.

Also, a sheath fluid such as distilled water or physiological saline solution is put into a sheath fluid container 14. The sample fluid container 16 and the sheath fluid container 14 each are pressurized by a pressurizing mechanism, not shown. In a flow cell 4, the sample fluid is wrapped in the sheath fluid and converged into a fine flow by the laminar sheath flow principle, and passes through the substantially central portion of the through-flow portion in the flow cell 4. At this time, the individual latexes contained in the sample fluid are separated and flow one particle by one or one lump by one. A laser light emitted from a laser source 1 is converged into an arbitrary shape by a set of cylindrical lenses 2 and 3 whose directions of bus line are the direction of the through-flow portion and orthogonal to the direction of the through-flow portion and is applied to the flow of the latexes. The shape of the light beam applied to the latexes should preferably be an elliptical shape oblong relative to the flow. This is for the purpose of causing the light beam to be applied to the latexes with a uniform strength even if the positions of the flows of the individual latexes fluctuate.

Figure 1B:
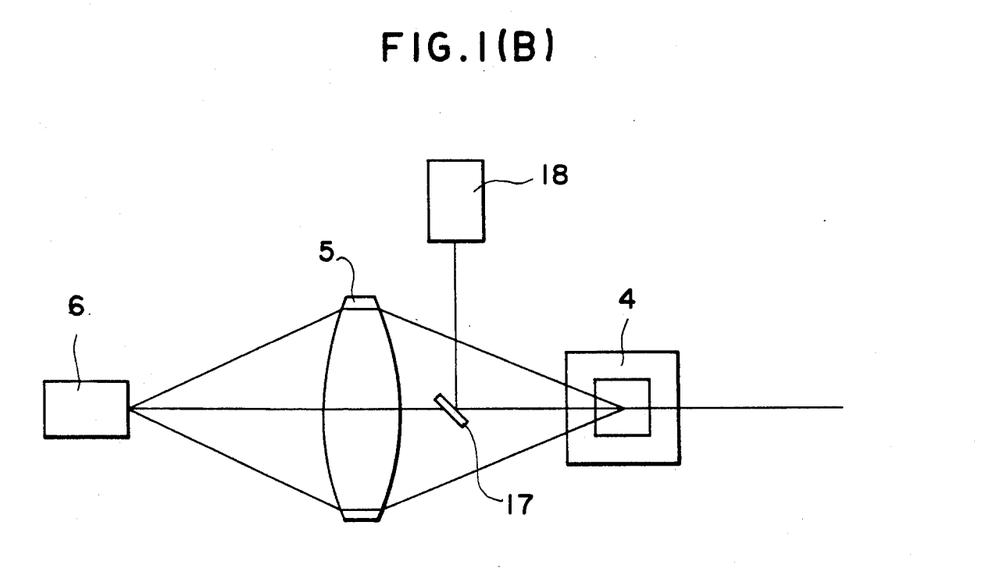
FIG. 1(B) shows the construction of a light receiving optical system when it receives transmitted light.
Figure 1C:
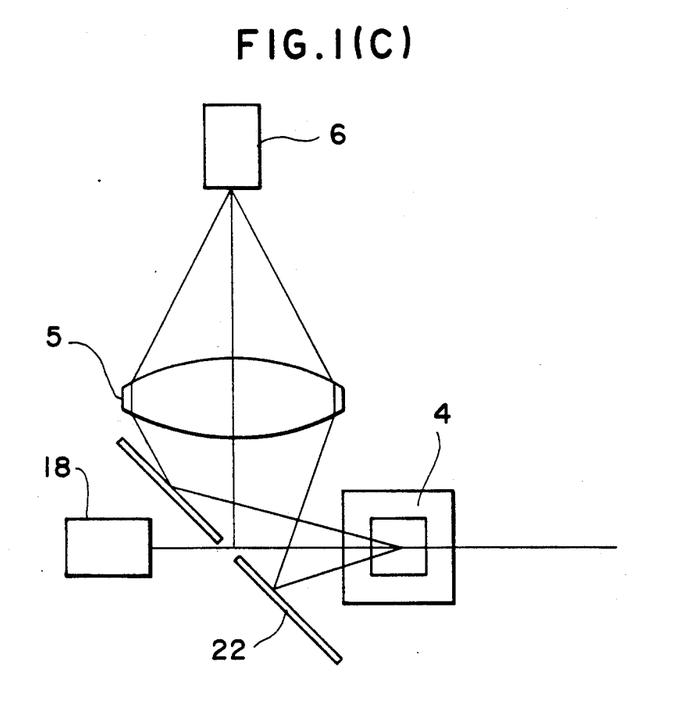
FIG. 1(C) shows a modification of the light receiving optical system of FIG. 1(B).

When the light beam is applied to the latexes, scattered lights are produced. Of the scattered lights, forward scattered light produced in the forward direction of the optical path is received by a condensing lens 5 and a photodetector 6. In order to prevent the applied light beam from directly entering the photodetector 6, a light-absorbing stopper 17 is provided in the optical path forwardly of the condensing lens 5, and the direct light from the irradiating light source and the transmitted light transmitted through the carriers are removed. Thus, only the scattered light from the carriers can be received. Where the transmitted light transmitted through the carriers is necessary as will be described later, the stopper 17 is obliquely provided as a reflective small mirror in the optical path as shown in FIG. 1(B), and the transmitted light can be obtained by the light reflected by the small mirror 17 being received by a photodetector 18. Alternatively, an apertured mirror 22 may be obliquely provided as shown in FIG. 1(C) and scattered light reflected thereby may be received by the condensing lens 5 and the photodetector 6 and transmitted light transmitted through the aperture may be received by a photodetector 18.

Also, of said scattered lights, laterally scattered light produced in the lateral direction orthogonal to the optical path is condensed by a condensing lens 7, is reflected by a dichroic mirror 8 and is received by a photodetector 11. Generally, the direction in which the laterally scattered light is received is often the orthogonal direction as in the present embodiment, whereas this is not restrictive, but may be, for example, a direction of 45 degrees or a direction of 60 degrees. Also, where the latexes are fluorescence-dyed, weak fluorescence produced with the scattered lights is received and therefore, of the fluorescence condensed by the condensing lens 7 and passed through the dichroic mirror 8, green fluorescence is detected by a set of dichroic mirror 9 and a photodetector 12 and red fluorescence is detected by a set of total reflection mirror 10 and photodetector 13. Although not shown in FIG. 1(A), a band-pass filter for passing only a light of the detected wavelength range therethrough is installed short of each photodetector. When the signals of the photodetectors 6, 11, 12 and 13 and the aforedescribed transmitted light are to be detected, the signal of the photodetector 18 is input to a calculation circuit 15, where calculation of particle analysis is effected.

In the sample fluid container 16, as previously described, a plurality of kinds of latexes A, B and C of different absorbances sensitized by the particular antibodies a, b and c, respectively, are mixedly present and a sample in which a specimen sample (for example, man's serum) is added thereto and the reaction time and concentration are appropriately adjusted is contained as a sample fluid. Of these latexes A, B and C, those of the same kind are equal in both of absorbance and size. The sizes of the latexes of different kinds may be the same or different from each other. Where an antigen uniquely coupled to the antibodies a, b and c sensitized by the respective latexes is contained in the serum, an antigen-antibody reaction occurs and the latexes of the same kind are coupled to each other through the antigen to form condensed lumps. When the antigen desired is not present, condensation does not occur and the latexes remain as single pieces.

Figure 2:
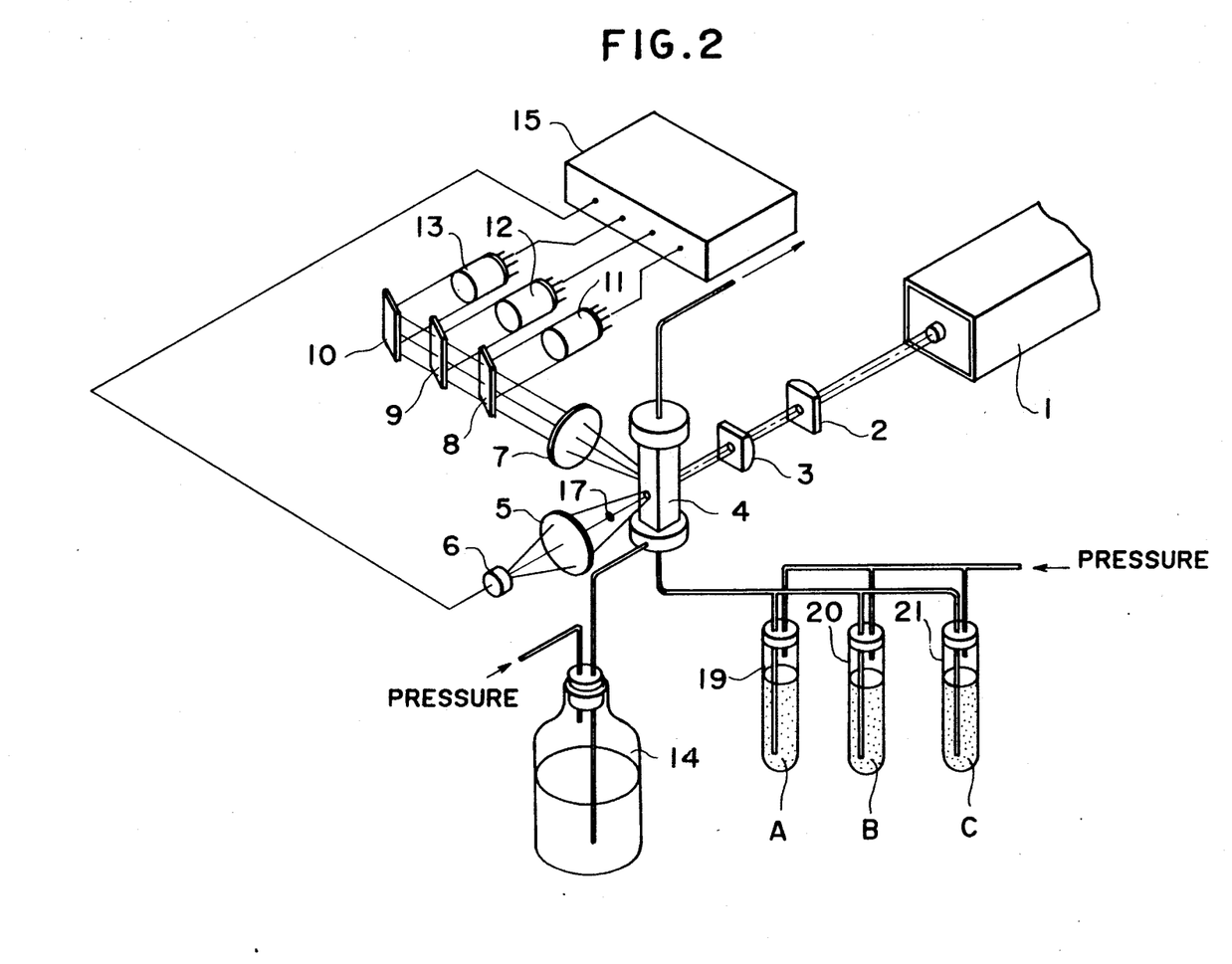
FIG. 2 shows a more preferable form of the embodiment of the present invention.

FIG. 2 shows the construction of a more preferable form of the specimen inspecting apparatus of the present invention. In FIG. 2, reference numerals similar to those in FIG. 1(A) designate similar members. In FIG. 1, the plurality of kinds of latexes A, B and C differing in absorbance are mixedly put into a sample fluid container, but as shown in FIG. 2, latexes A, B and C of different kinds are discretely put into different sample fluid containers 19, 20 and 21, and by applying a pressure in common to these sample fluid containers 19, 20 and 21, the latexes forced out merge at the through-flow portion and flow through the flow cell 4 one particle by one or one lump by one. Thus, the latexes do not mix together until immediately before they flow into the measuring portion and therefore, the possibility of the respective antigen-antibody reactions influencing each other can be minimized.

The basic idea of a method of applying a light beam to the sample fluid flowing in the above-described apparatus and measuring a plurality of kinds of antigen-antibody reactions at a time from the strength of the forward scattered light and the strength of the laterally scattered light will now be described with reference to FIGS. 3 to 5.

Figure 3:
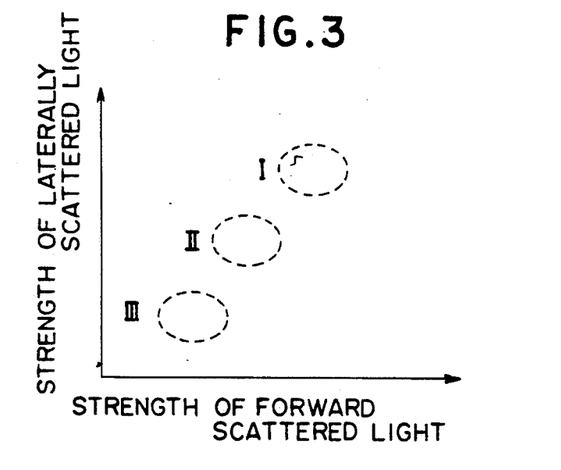
FIGS. 3 to 5 basically illustrate the inspecting method of the present invention.
Figure 4:
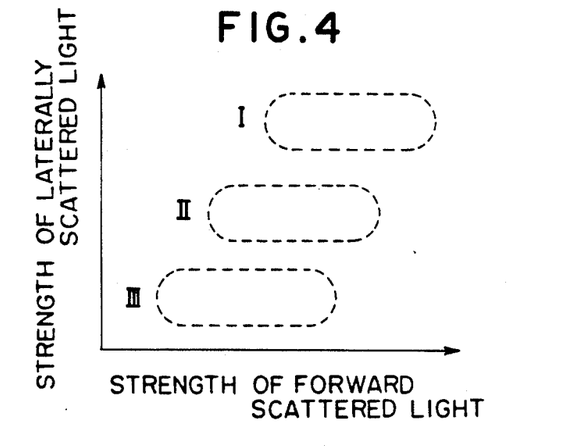
Figure 5:
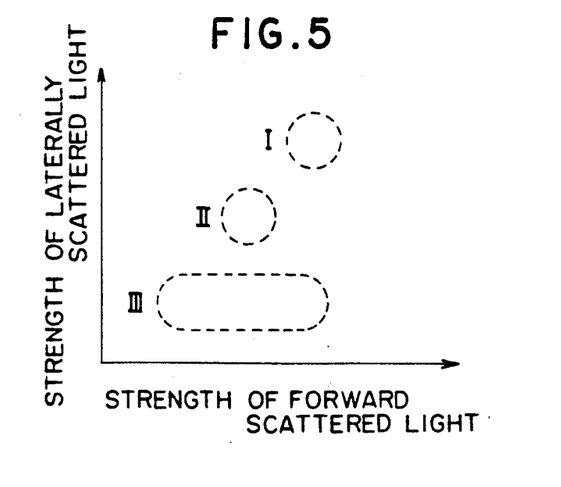

FIGS. 3 to 5 show an example when measurement data are indicated by a cytogram with the strength of the laterally scattered light and the strength of the forward scattered light plotted as the vertical axis and the horizontal axis, respectively, where three kinds of latexes A, B and C differing in absorbance are used, and the ranges encircled by dotted lines indicate the ranges in which the measurement data as plotted collect.

It is generally known that when a light is applied to minute particles such as latexes, the information of the optical characteristic such as the absorbance of the particles is chiefly included in the strength of the laterally scattered light and the information of the particle size is chiefly included in the strength of the forward scattered light. Consequently, the difference in absorbance between the latexes appears in the strength of the laterally scattered light and therefore, the distinction between the kinds of the latexes is judged by the latexes being separated in the direction of the vertical axis of the cytogram. Also, the larger the particle diameter of the particles to be examined, the greater is the strength of the forward scattered light and therefore, when an antigen-antibody reaction occurs and condensed lumps of the latexes are formed, the apparent latex diameter increases and therefore, the strength of the forward scattered light becomes great and the range widens in the direction of the horizontal axis of the cytogram. FIG. 3 shows the distribution when the desired antigen is not present in the serum and the antigen-antibody reaction does not occur at all, and by the kinds A, B and C of the latexes, plotting is effected with the latexes separated into narrow ranges indicated by the dotted lines of groups I, II and III. FIG. 4 shows the cytogram when antigens uniquely coupled to three kinds of antibodies a, b and c are all present, and since the latexes are condensed and the number of particle lumps of large size is increased, plotting is effected in the range widening in the direction of the horizontal direction in the distribution graph, as indicated by the dotted lines of groups I, II and III. FIG. 5 is the cytogram when only the latex C causes an antigen-antibody reaction and condensed lumps are produced, and only the group III widens in the direction of the horizontal direction. That is, it can be judged that the antigens a and b are not present in the specimen sample and only the antigen c is present. Thus, discrete antigen-antibody reactions appear separately on the distribution graph and therefore, the presence of a plurality of antigens can be judged by one measurement at a time. Also, by seeing the size of the particle lumps, a rough amount of antigen can be grasped.

In the present embodiment, three kinds of latexes differing in absorbance are used, but it is also possible to measure four or more kinds at a time, and if the number of kinds is two, distinction can be made more clearly.

In the present embodiment, the latexes are sensitized by the antibody, but conversely, the latexes may be sensitized by an antigen and inspection may be done with a sample to be examined including an antibody added thereto, whereby it is also possible to discriminate a particular antibody.

Further, in the present embodiment, the difference in absorbance between the carriers is discriminated from the laterally scattered light output, but the laterally scattered light includes the information of optical characteristics such as the degree of light transmission which is in close relation with absorbance, the degree of light refraction and the degree of light reflection of the carrier surface. Consequently, even if use is made of a plurality of kinds of carriers differing in these optical characteristics, similar measurement can be accomplished by an apparatus construction similar to that described above.

In the foregoing, description has been made of the basic idea of the method of detecting a plurality of kinds of antigen-antibody reactions at one time by the use of carriers differing in absorbance. Strictly, however, the clear output as shown in FIGS. 3 to 5 is not provided. This is considered to be because the strength of the forward scattered light and the strength of the laterally scattered light do not have entirely discrete types of information, but have a correlation therebetween.

FIGS. 6 to 8 and 12 show the results of the measurement effected on the three kinds of latexes A, B and C of the same particle diameter and differing in absorbance described in the previous embodiment sensitized by discrete antibodies a, b and c. When only the latex A of the three kinds of latexes is caused to flow, the histogram of the forward scattered light by particles condensed by the antigen-antibody reaction is represented as shown in FIG. 6(A). In the figure, the horizontal axis represents the strength of the forward scattered light FS received by the photodetector 6, and the vertical axis represents the number N of particles. Since the strength of the forward scattered light depends on the particle diameter, the latexes are varied in apparent size by condensation and are indicated on the graph while being separated as $I_1$, $I_2$ and $I_3$. The numbers of condensed latexes are considered to be one, two and three, respectively. FIG. 6(B) is a histogram of the laterally scattered light, in which the horizontal axis represents the strength of the laterally scattered light received by the photodetector 11 and the vertical axis represents the number N of particles. Since the strength of the laterally scattered light is varied by the absorbance of particles, the absorbance of condensed lumps is varied by condensation and is indicated on the graph while being separated as $J_1$, $J_2$ and $J_3$. FIG. 6(C) is a cytogram showing these two histograms in a lump. In the figure, the horizontal axis represents the strength of the laterally scattered light and the vertical axis represents the strength of the forward scattered light. $I_1$ is FIG. 6(A) and $J_1$ in FIG. 6(B) are by the same particle, and likewise, the sets of $I_2$, $J_2$ and $I_3$, $J_3$ are by the same lump of particles. Consequently, there appear on the cytogram three groups such as a group of particles in which the laterally scattered light is $J_1$ and the forward scattered light is $I_1$, a group of particles in which the laterally scattered light is $J_2$ and the forward scattered light is $I_2$, and a group of particles in which the laterally scattered light is $J_3$ and the forward scattered light is $I_3$. This can be judged as the particles being in the condensed states of one, two and three particles, respectively. The foregoing has described the case where the antigen-antibody reaction has occurred and particles have been condensed, but when the desired antigen is not present and condensation does not occur, $I_2$, $J_2$, $I_3$ and $J_3$ by condensation do not appear on the cytogram, but only $I_1$ and $J_1$ appear. When four or more large condensed lumps are present, they appear on a broken line linking the groups of FIG. 6(C) together. By seeing the groups appearing on the cytogram as described above, the presence of the antigen to be sought after can be detected.

Figure 7A:
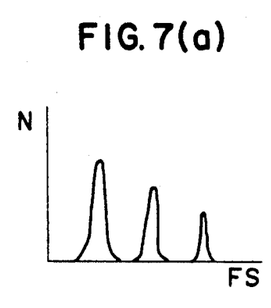
Figure 7B:
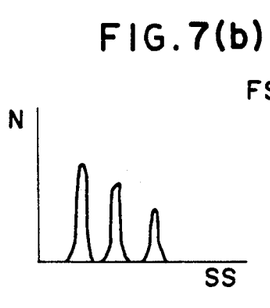
Figure 7C:
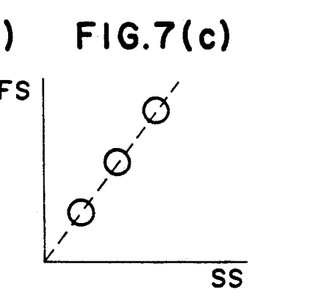
Figure 8A:
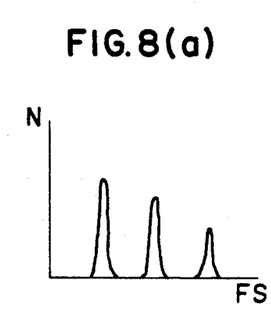
Figure 8B:
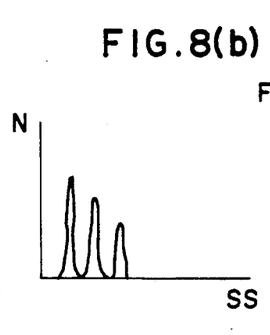
Figure 8C:
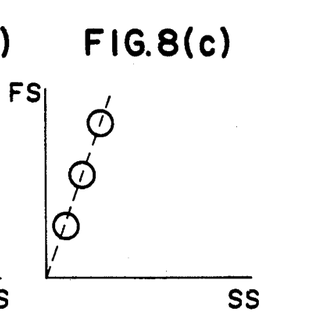

Likewise, measurement is effected by the use of other kinds of latexes B and C having the same particle diameter as said latex A but differing in absorbance from said latex A, and when the antigens b and c are present, there can be obtained histograms and cytograms as shown in FIGS. 7 and 8, respectively.

Figure 6A:
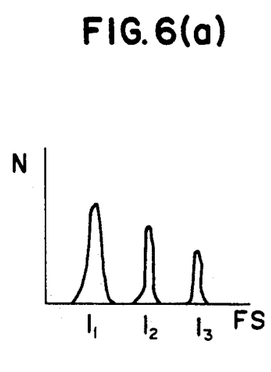
Figure 6B:
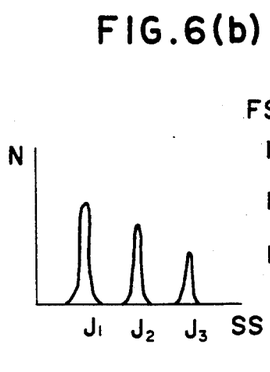
Figure 6C:
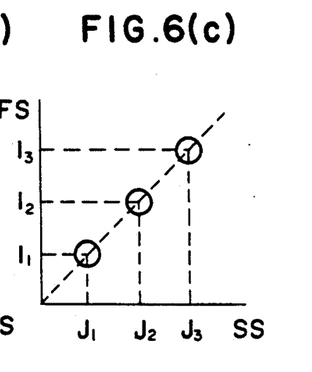
Figure 12:
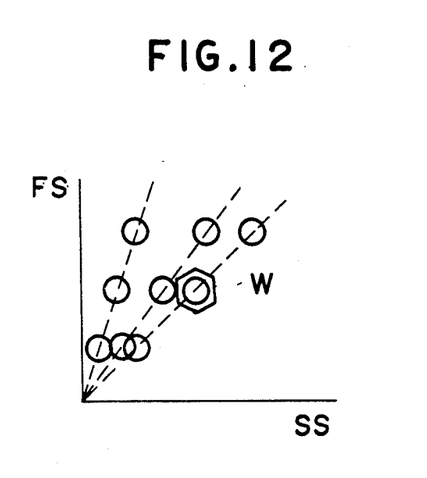

FIG. 12 is a cytogram in which the cytograms of FIGS. 6(C), 7(C) and 8(C) are arranged into one, and corresponds to FIGS. 3 to 5. In this figure, the axes of the strength of the forward scattered light FS and the strength of the laterally scattered light SS are replaced with each other. In the cytogram of FIG. 12, the group lying on each broken line is the information regarding the same antigen (antibody). FIG. 12 shows the result when the antigens for three kinds of antibodies a, b and c are all present. In FIG. 12, the point of intersection at which FS and SS both assume the same value does not substantially exist and therefore, the kind and amount of the antigen can be specified.

It is a popularly used method to effect window processing indicated at W to thereby examine the number (count number) of particles present in the window. Now, referring to FIG. 12, there are portions in which groups are close to one another on the cytogram, and this is because latexes having the same size but differing in absorbance, that is, latexes which are substantially equal in the strength of the forward scattered light and differ in only the strength of the laterally scattered light are selected as the latexes A, B and C. This leads to the problem that the window processing becomes difficult.

So, let it be assumed that the latexes A, B and C differ in both absorbance and particle diameter. Specifically, by using three kinds of latexes A, B and C which are greater in particle diameter as absorbance is greater, design is made such that each group appears widely on the cytogram.

Figure 9A:
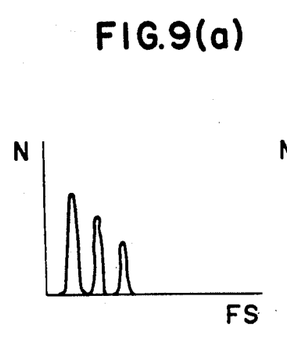
Figures 9B, 9C:
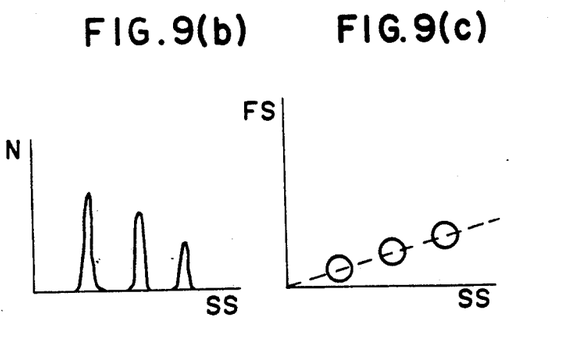
Figure 10A:
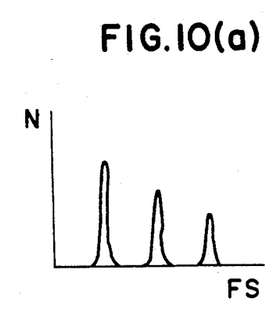
Figure 10B:
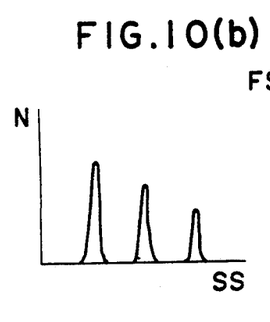
Figure 10C:
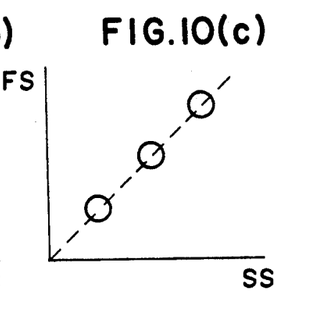
Figure 11A:
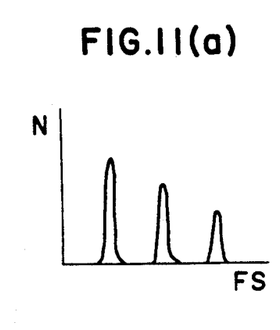
Figures 11B, 11C:
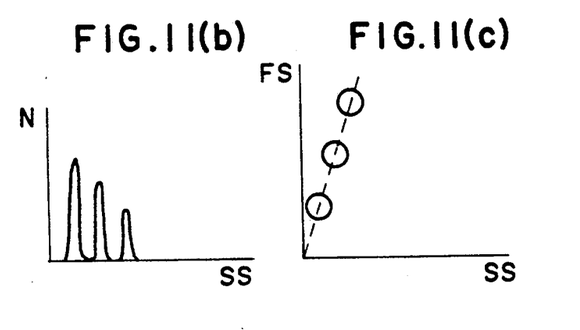
Figure 13:
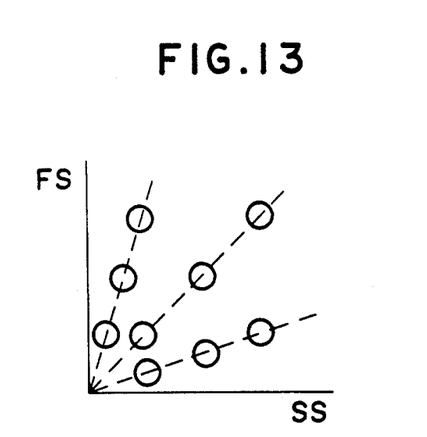

FIG. 9 shows the cytograms by a latex which is small in both particle diameter and absorbance, that is, a latex in which the strength of the forward scattered light FS is small and the strength of the laterally scattered light SS is of a great output, FIG. 10 shows the cytograms by a latex in which FS is great and SS is also great, and FIG. 11 shows the cytograms by a latex in which FS is great and SS is small. By using a combination of such three kinds of latexes A, B and C, the resultant cytogram is a cytogram as shown in FIG. 13 wherein respective groups are widely separated and the window processing is easy to do.

In the embodiments described hitherto, the output of the laterally scattered light is used to examine the absorbance of the carriers, but the information of the optical characteristics such as the absorbance, etc. of the carriers is included also in the transmitted light of the light applied to the carrier. Consequently, if the strength of the transmitted light is measured, the kinds of the carriers can be distinguished also from the measured strength of the transmitted light. As previously described, in the apparatus of FIG. 1(A) or 2, the forward scattered light receiving system is made into a construction as shown in FIG. 1(B) or 1(C), whereby the transmitted light can be detected. Consequently, by effecting an analysis similar to that described above in the calculation circuit 15 by the use of the transmitted light instead of the laterally scattered light, there can be obtained a substantially similar measurement result.

I claim:

1. A specimen inspecting method comprising the following steps:
   (a) making a sample by mixing a reagent with a specimen sample, said sample comprising a first carrier group of uniform size coated with a first antibody or antigen and provided with a first optical characteristic for an irradiating light and a second carrier group of uniform size coated with a second antibody or antigen and provided with a second optical characteristic differing from said first optical characteristic for the irradiating light, wherein each said first and second carriers condense with an objective antigen or antibody in said specimen sample to form a condensed state;
   (b) applying a light to the individual carriers in said sample;
   (c) detecting forward scattered light scattered from the carriers to which the light is applied;
   (d) detecting transmitted light transmitted through the carriers to which the light is applied or laterally scattered light scattered from the carriers to which the light is applied;
   (e) discriminating the condensed state of said carriers and the kinds of the carriers on the basis of the detection results of step (c) and step (d); and
   (f) inspecting first and second antigens or antibodies uniquely coupled to the first and second antibodies or antigens in said specimen sample.

2. A specimen inspecting method according to claim 1, wherein said optical characteristic is the absorbance of the carriers.

3. A specimen inspecting method according to claim 1, wherein said optical characteristic is the degree of light transmission of the carriers.

4. A specimen inspecting method according to claim 1, wherein said optical characteristic is the degree of light refraction of the carriers.

5. A specimen inspecting method according to claim 1, wherein said optical characteristic the degree of light reflection of the carriers.

6. A specimen inspecting method according to claim 3, wherein said first carrier group is large in size and also great in absorbance relative to said second carrier group.

7. A specimen inspecting apparatus comprising:
   means for flowing a sample in an inspecting position, said sample made by mixing a first carrier group of uniform size coated with a first antibody or antigen and provided with a first optical characteristic for an irradiating light and a second carrier group of uniform size coated with a second antibody or antigen and provided with a second optical characteristic differing from said first optical characteristic for the irradiating light with a specimen sample, wherein each said first and second carriers condense with an objective antigen or antibody in said specimen sample to form a condensed state;
   light applying means for applying a light to the individual carriers in said sample flowing in said inspecting position;
   first light receiving means for receiving forward scattered light scattered from said carriers;
   second light receiving means for receiving transmitted light through said carriers or laterally scattered light scattered from said carriers; and
   calculating means for discriminating the condensed state of said carriers and the kinds of the carriers from output values obtained by said first and second light receiving means and effecting the inspection of first and second antigens or antibodies uniquely coupled to said first and second antibodies or antigens in said specimen sample.

8. A specimen inspecting apparatus according to claim 7, wherein said optical characteristic is the absorbance of the carriers.

9. A specimen inspecting apparatus according to claim 7, wherein said optical characteristic is the degree of light transmission of the carriers.

10. A specimen inspecting apparatus according to claim 7, wherein said optical characteristic is the degree of light refraction of the carriers.

11. A specimen inspecting apparatus according to claim 7, wherein said optical characteristic is the degree of light reflection of the carriers.

12. A specimen inspecting apparatus according to claim 7, wherein sample containers for containing the first and second carrier groups, respectively, are prepared discretely.

13. A specimen inspecting apparatus according to claim 8, wherein said first carrier group is large in size and also great in absorbance relative to said second carrier group.

14. The specimen inspecting apparatus according to claim 7, wherein said inspecting position is in a flow cell and each of said carrier is transported in the flow cell by laminar sheath flow.

15. The specimen inspecting apparatus according to claim 7, wherein said light applying means includes a laser light source.

16. The specimen inspecting apparatus according to claim 15, wherein said light applying means includes an optical system for imaging a laser beam projected from said laser light source to said inspecting position.

17. The specimen inspecting apparatus according to claim 7, further comprising output means for outputting a calculation performed by said calculating means.

18. The specimen inspecting apparatus according to claim 17, further comprising means to statistically process and to output to said output means the data of forward scattered light obtained by said first light receiving means and the data of transmitted light or laterally scattered light.

19. The specimen inspecting apparatus according to claim 18, wherein said means to statistically process is a cytogram.

20. The specimen inspecting apparatus according to claim 18, wherein said mean to statistically process is a histogram.

21. A specimen inspecting reagent for simultaneously inspecting a first and second objective antigen or antibody by flow cytometry comprising:
 a first carrier group coated with a first antibody or antigen which uniquely responds to said first objective antigen or antibody, said first carrier being coupled to each other when condensed with said first objective antigen or antibody, said first carrier group having a first optical characteristic to a projection light; and
 a second carrier group coated with a second antibody or antigen which uniquely responds to said second objective antigen or antibody, said second carrier being coupled to each other when condensed with said second objective antigen or antibody, said second carrier group having a second optical characteristic different from said first optical characteristic to the projection light, wherein said first carrier group and said second carrier group differ from each other in average size.

22. The specimen inspecting reagent according to claim 21, wherein said carrier is latex particles.

23. The specimen inspecting reagent according to claim 21, wherein said first and second carrier groups have different light absorbency.

24. The specimen inspecting reagent according to claim 21, wherein said first and second carrier groups have different light transmittability.

25. The specimen inspecting reagent according to claim 21, wherein said first and second carrier groups have different light refractivity.

26. The specimen inspecting reagent according to claim 21, wherein said first and second carrier groups have different light reflectivity.

27. The specimen inspecting reagent according to claim 21, wherein the first carrier group and the second carrier groups differ from each other in average size of particle.

28. A specimen inspecting reagent for simultaneously inspecting a first and second objective antigen or antibody by flow cytometry comprising:
 a first carrier group coated with first antibody or antigen which uniquely responds to said first objective antigen or antibody, said first carriers being coupled to each other when condensed with said first objective antigen or antibody; and
 a second carrier group coated with second antibody or antigen which uniquely responds to said second objective antigen or antibody, said second carriers being coupled to each other when condensed with said second objective antigen or antibody, said second carrier group having a characteristic of at least one of transmission light strength and lateral scattered light strength to the projection light, which said characteristic is different from a corresponding characteristic of said first carrier group, wherein said first carrier group and said second carrier group differ from each other in average size.

29. The specimen inspecting reagent according to claim 28, wherein said carrier consists of latex particles.

30. The specimen inspecting reagent according to claim 28, wherein said first and second carrier groups have different light absorbency.

31. The specimen inspecting reagent according to claim 28, wherein said first and second carrier groups have different light transmittability.

32. The specimen inspecting reagent according to claim 28, wherein said first and second carrier groups have different light refractivity.

33. The specimen inspecting reagent according to claim 28, wherein said first and second carrier groups have different light reflectivity.

34. A specimen inspecting method, comprising the following steps:
 (a) producing a sample by mixing a first carrier group and a second carrier group with a specimen sample, said first carrier group coated with first antibody or antigen which uniquely responds to a first objective antigen or antibody, said first carriers being coupled to each other when condensed with said first objective antigen or antibody to form a condensed state and having a first optical characteristic to a projection light, said second carrier group coated with second antigen or antibody which uniquely responds to a second objective antigen or antibody, and said second carriers coupled to each other when condensed with said second objective antigen or antibody to form a condensed state and having a second optical characteristic different from the first optical characteristic to the projection light, wherein said first carrier group and said second carrier group differ from each other in average size;
 (b) optically measuring each carrier contained in the sample produced in said step (a);
 (c) discriminating between the condensed state and kind of said carriers on the basis of the output of step (b); and
 (d) inspecting the first and second objective antigen or antibody based on the discriminated condensed state and kind of said carriers.

35. The specimen inspecting method according to claim 34, wherein said carrier is latex particles.

36. The specimen inspecting method according to claim 34, wherein said first and second carrier groups have different light absorbency.

37. The specimen inspecting method according to claim 34, wherein said first and second carrier groups have different light transmittability.

38. The specimen inspecting method according to claim 34, wherein said first and second carrier groups have different light refractivity.

39. The specimen inspecting method according to claim 34, wherein said first and second carrier groups have different light reflectivity.

40. The specimen inspecting method according to claim 34, wherein said inspection effected in said step (c) is carried out by statistically processing a large number of measured data.

41. The specimen inspecting method according to claim 40, wherein said statistical processing step includes conducting a cytogram processing step.

42. The specimen inspecting method according to claim 40, wherein said statistical processing step includes conducting a histogram processing step.

43. A specimen inspecting method, comprising the following steps:
   (a) producing a sample by mixing a first carrier group and a second carrier group with a specimen sample, said first carrier group coated with a first antibody or antigen which uniquely responds to a first objective antigen or antibody, said first carriers being coupled to each other when condensed with said first objective antigen or antibody to form a condensed state, said second carrier group coated with a second antibody or antigen which uniquely responds to a second objective antigen or antibody, said second carriers being coupled to each other when condensed with said second objective antigen or antibody to form a condensed state, said second carrier group having a characteristic of at least one of transmission light strength and lateral scattered light strength to the projection light, which is different from the characteristic of said first carrier group, wherein said first carrier group and said second carrier group differ from each other in average size;
   (b) optically measuring each carrier contained in the sample produced in said step (a);
   (c) discriminating between the condensed state and kind of said carriers on the basis of the output of step (b); and
   (d) inspecting the first and second objective antigen or antibody based on the discriminated condensed state and kind of said carriers.

44. The specimen inspecting method according to claim 43, wherein said carrier consists of latex particles.

45. The specimen inspecting method according to claim 43, wherein said first and second carrier groups have different light absorbency.

46. The specimen inspecting method according to claim 41, wherein said first and second carrier groups have different light transmittability.

47. The specimen inspecting method according to claim 43, wherein said first and second carrier groups have different light refractivity.

48. The specimen inspecting method according to claim 43, wherein said first and second carrier groups have different light reflectivity.

49. The specimen inspecting method according to claim 43, wherein said inspection effected in said step (c) is carried out by statistically processing a large number of measured data.

50. The specimen inspecting method according to claim 40, wherein said statistical processing step includes conducting a cytogram processing step.

51. The specimen inspecting method according to claim 49, wherein said statistical processing step includes conducting a histogram processing step.

52. An apparatus for inspecting a specimen, comprising:
   (a) supplying means for supplying to a measuring position a sample produced by mixing a first carrier group and a second carrier group with a specimen sample, said first carrier group coated with a first antibody or antigen which uniquely responds to a first objective antigen or antibody, said first carriers being coupled to each other when condensed with said first objective antigen or antibody and having a first optical characteristic to a projection light, said second carrier group coated with second antigen or antibody which uniquely responds to a second objective antigen or antibody, said second carriers being coupled to each other when condensed with second objective antigen or antibody and having a second optical characteristic different from the first optical characteristic to the projection light, wherein said fist carrier group and said second carrier group differ from each other in average size;
   (b) measuring means for optically measuring each carrier contained in the sample supplied by said supplying means; and
   (c) calculation means for discriminating between the condensed state and kind of said carriers on the basis of the output of said measuring means; and
   (d) means for inspecting the first and second desired antigen or antibody based on the discriminated condensed state and kind of said carriers.

53. The apparatus for inspecting a specimen, according to claim 52, wherein said inspecting position is in a flow cell and each said carrier is transported in the flow cell by laminar sheath flow.

54. The apparatus for inspecting a specimen according to claim 52, wherein said light applying means includes a laser light source.

55. The apparatus for inspecting a specimen, according to claim 52, wherein said measuring means includes a sensor for receiving a scattered light from said inspecting position.

56. The apparatus for inspecting a specimen, according to claim 52, further comprising output means for outputting a result calculated by said calculation means.

57. The apparatus for inspecting a specimen, according to claim 56, wherein said output means output a result based on statistical processing of a large number of data obtained by said measuring means.

58. The apparatus for inspecting a specimen, according to claim 57, wherein output means outputs a result based on said statistical processing with a cytogram program.

59. The apparatus for inspecting a specimen, according to claim 57, wherein output means outputs a result based on said statistical processing with a histogram program.

60. The apparatus for inspecting a specimen, according to claim 52, further comprising a first sample container means for containing said first carrier; a second sample container means for containing said second carrier; and a supply passage for introducing said first carrier in said first sample container and said second carrier in said second sample container respectively to a common inspecting position.

61. An apparatus for inspecting a specimen, comprising:
   (a) supplying means for supplying to a measuring position a sample produced by mixing a first carrier group and a second carrier group with a specimen sample, said first carrier group coated with a first antibody or antigen which uniquely responds to a first objective antigen or antibody, said first carriers being coupled to each other when condensed with said first objective antigen or antibody and said second carrier group coated with a second antigen or antibody which uniquely responds to a second objective antigen or antibody, said second carriers being coupled to each other when condensed with said second objective antigen or antibody and having a characteristic of at least one of transmission light strength and lateral scattered light strength to the projection light, which is different from the characteristic of said first carrier group, wherein said first carrier group and said second carrier group differ from each other in average size of particles;

(b) measuring means for optically measuring each carrier contained in the sample supplied by said supplying means; and (c) calculation means for discriminating between the condensed state and kind of said carriers on the basis of the output of said measuring means; and (d) means for inspecting the first and second desired antigen or antibody based on the discriminated condensed state and kind of said carriers.

62. The apparatus for inspecting a specimen, according to claim 61, wherein said inspecting position is in a flow cell and each said carrier is transported in the flow cell by laminar sheath flow.

63. The apparatus for inspecting a specimen according to claim 61, wherein said light applying means includes a laser light source.

64. The apparatus for inspecting a specimen, according to claim 61, wherein said measuring means includes a sensor for receiving a scattered light form said inspecting position.

65. The apparatus for inspecting a specimen, according to claim 61, further comprising output means for outputting a result calculated by said calculation means.

66. The apparatus for inspecting a specimen, according to claim 65, wherein said output means outputs a result based on statistical processing of a large number of data obtained by said measuring means.

67. The apparatus for inspecting a specimen, according to claim 66, wherein output means outputs a result based on said statistical processing with a cytogram program.

68. The apparatus for inspecting a specimen, according to claim 66, wherein output means outputs a result based on said statistical processing with a histogram program.

69. An apparatus for inspecting a specimen, according to claim 61, further comprising a first sample container means for containing said first carrier; a second sample container means for containing said second carrier; and a supply passage for introducing said first carrier in said first sample container and said second carrier in said second sample container respectively to a common inspecting position.

* * * * *

UNITED STATES PATENT AND TRADEMARK OFFICE
CERTIFICATE OF CORRECTION

PATENT NO. : 5,162,863
DATED : November 10, 1992
INVENTOR(S) : YUJI ITO

It is certified that error appears in the above-indentified patent and that said Letters Patent is hereby corrected as shown below:

TITLE PAGE

AT [56] REFERENCES CITED

Foreign Patent Documents, insert,
--62-81567  4/1987  Japan--.

COLUMN 1

Line 45, "formed" should read --become--.

COLUMN 6

Line 13, "is" should read --in--.

COLUMN 8

Line 62, "carrier" should read --carriers--.

COLUMN 9

Line 16, "mean" should read --means--.
Line 54, "groups" should read --group--.

COLUMN 11

Line 1, "(c)" should read --(d)--.
Line 55, "(c)" should read --(d)--.

UNITED STATES PATENT AND TRADEMARK OFFICE
CERTIFICATE OF CORRECTION

PATENT NO. : 5,162,863
DATED : November 10, 1992
INVENTOR(S) : YUJI ITO

It is certified that error appears in the above-indentified patent and that said Letters Patent is hereby corrected as shown below:

COLUMN 12

Line 13, "fist" should read --first--.
Line 40, "output a" should read --outputs a--.
Line 44, "output means" should read --said output means--.
Line 48, "output means" should read --said output means--.

COLUMN 14

Line 3, "form" should read --from--.
Line 13, "output means" should read --said output means--.
Line 17, "output means" should read --said output means--.

Signed and Sealed this

Fourth Day of January, 1994

Attest:

BRUCE LEHMAN

Attesting Officer    Commissioner of Patents and Trademarks